United States Patent [19]

Liotta, Jr.

[11] Patent Number: 5,206,408
[45] Date of Patent: Apr. 27, 1993

[54] PROCESS FOR THE PREPARATION OF UNSYMMETRIC DIALKYL CARBONATES

[75] Inventor: Frank J. Liotta, Jr., Collegeville, Pa.

[73] Assignee: Arco Chemical Technology, L.P., Wilmington, Del.

[21] Appl. No.: 886,719

[22] Filed: May 21, 1992

[51] Int. Cl.$^5$ .................... C07C 69/96; C07C 68/00
[52] U.S. Cl. .................... 558/277; 558/270; 558/260
[58] Field of Search .................... 558/277, 270

[56] References Cited

U.S. PATENT DOCUMENTS 3,227,741  1/1966  Fenton ................... 558/277
3,642,858  2/1972  Frevel et al. ........... 558/277
4,181,676  1/1980  Buysch et al. .......... 558/277 X Primary Examiner—Floyd D. Higel
Attorney, Agent, or Firm—Jonathan L. Schuchardt

[57] ABSTRACT

Basic cesium compounds are effective transesterification catalysts for the conversion of symmetric dialkyl carbonates to unsymmetric dialkyl carbonates. Crown ethers, polyalkylene glycols, and polyalkylene glycol ethers are useful cocatalysts for the process. Methyl tert-butyl carbonate and methyl tertamyl carbonate, useful octane enhancers for gasoline, can be prepared using the process.

22 Claims, No Drawings

PROCESS FOR THE PREPARATION OF UNSYMMETRIC DIALKYL CARBONATES

FIELD OF THE INVENTION

The invention relates to the preparation of dialkyl carbonates, and more particularly, to the preparation of unsymmetric dialkyl carbonates by base-catalyzed transesterification of symmetric carbonic acid diesters (symmetric carbonates). Certain unsymmmetric carbonates, such as methyl tert-butyl carbonate (MTBC) and methyl tert-amyl carbonate, are useful octane enhancers for fuels.

BACKGROUND OF THE INVENTION

Few practical methods for the preparation of unsymmetric dialkyl carbonates are known. A potentially useful approach is to react a symmetric dialkyl carbonate with an alcohol in the presence of a transesterification catalyst. Known transesterification catalysts include Lewis acids, soluble tin compounds, cyclic amines, N,N-dimethylaminopyridine, organotitanates, and acidic ion-exchange resins.

Unfortunately, the synthesis of unsymmetric dialkyl carbonates, particularly those derived from the reaction of a symmetric dialkyl carbonate and a tertiary alcohol, is often hampered by poor reactivity, difficult catalyst recovery, and/or unwanted side reactions. For example, I have found that the preparation of methyl tert-butyl carbonate from dimethyl carbonate and tert-butyl alcohol in the presence of "Amberlyst 15" resin (a product of Rohm and Haas Company) is unsatisfactory because tert-butyl alcohol rapidly dehydrates to isobutylene under these conditions.

Inorganic carbonates, alcoholates, and hydroxides also catalyze transesterifications of dialkyl carbonates (see, for example, European Patent Application No. 0274953 and *Ind. Enq. Chem. Res.* 27 (1988) 1565; 28 (1989) 881). Crown ethers or polyethylene glycols can be used in combination with the inorganic bases to enhance reactivity. Lithium, sodium, and potassium compounds are taught; cesium compounds are not taught. The target products are typically symmetric dialkyl carbonates.

U.S. Pat. No. 3,642,858 lists basic cesium compounds as suitable catalysts for the preparation of dialkyl carbonates from the reaction of cyclic carbonates (e.g., ethylene carbonate) with non-tertiary hydroxy-containing compounds. The products exemplified in the reference are all symmetric carbonates, and only sodium catalysts are shown.

I have found that basic lithium, potassium, and sodium compounds are generally unsatisfactory transesterification catalysts for the preparation of unsymmetric dialkyl carbonates from symmetric dialkyl carbonates, and that this is particularly true for the preparation of unsymmetric dialkyl carbonates derived in part from tertiary alcohols. In view of the value of certain unsymmetric dialkyl carbonates as octane enhancers for fuels, an improved synthesis of these compounds is needed.

SUMMARY OF THE INVENTION

An object of the invention is to provide an improved transesterification process for the preparation of unsymmetric dialkyl carbonates. Preferably, the process is well-suited to the preparation of unsymmetric dialkyl carbonates from symmetric dialkyl carbonates and tertiary alcohols.

The invention is a process for producing an unsymmetric dialkyl carbonate. The process comprises reacting a symmetric dialkyl carbonate with an alcohol in the presence of a basic cesium compound to produce the unsymmetric dialkyl carbonate. The process is especially suitable for the preparation of unsymmetric dialkyl carbonates derived from tertiary alcohols.

I have surprisingly discovered that, unlike basic lithium, sodium, and potassium compounds, basic cesium compounds effectively catalyze the synthesis of unsymmetric dialkyl carbonates from alcohols and symmetric dialkyl carbonates. The process of the invention is an effective route to unsymmetric dialkyl carbonates derived from tertiary alcohols, such as methyl tert-butyl carbonate.

DETAILED DESCRIPTION OF THE INVENTION

In the process of the invention, a symmetric dialkyl carbonate reacts with an alcohol in the presence of a basic cesium compound to give an unsymmetric dialkyl carbonate.

Any symmetric dialkyl carbonate can be used. Preferred symmetric dialkyl carbonates have the general formula RO—CO—OR, in which R is a linear, branched, or cyclic $C_1$-$C_{10}$ alkyl 9group. More preferred symmetric dialkyl carbonates have $C_1$-$C_4$ alkyl groups. Suitable symmetric dialkyl carbonates include, but are not limited to, dimethyl carbonate, diethyl carbonate, di-n-butyl carbonate, di-tert-butyl carbonate, di-n-octyl carbonate, and the like. Most preferred are dimethyl carbonate and diethyl carbonate, since the alcohols derived from these are typically easy to separate from the unsymmetric dialkyl carbonate products by distillation.

Alcohols useful in the invention are preferably $C_1$-$C_{20}$ linear, branched, and cyclic aliphatic and aromatic alcohols. More preferred alcohols are $C_1$-$C_{10}$ aliphatic alcohols. Particularly preferred are tertiary $C_4$-$C_6$ aliphatic alcohols. Suitable alcohols include, but are not limited to, methanol, ethanol, isopropanol, tert-butyl alcohol, tert-amyl alcohol, n-octyl alcohol, cyclohexanol, benzyl alcohol, and the like. Preferred alcohols are tert-butyl alcohol and tert-amyl alcohol.

The alcohol and symmetric dialkyl carbonate can be combined in any desired proportion. It is preferred, however to use an excess amount of the alcohol. A preferred alcohol:symmetric dialkyl carbonate ratio is within the range of about 2:1 to about 100:1; more preferred is the range from about 2:1 to about 20:1; most preferred is the range from about 4:1 to about 10:1.

A basic cesium compound catalyzes the process of the invention. Suitable basic cesium compounds include, for example, cesium, cesium hydride, cesium hydroxide, cesium alkoxides, cesium carboxylates, cesium carbonate, cesium bicarbonate, cesium oxide, and the like, and mixtures thereof. Cesium carbonate and cesium oxide are particularly preferred. Neutral cesium compounds, such as cesium oxalate, cesium chloride, and the like, are generally unsuitable for use in the process (see Comparative Examples 22-24.

The amount of basic cesium compound required is that sufficient to give satisfactory conversion to the unsymmetric carbonate within the desired reaction time. Generally, it is preferred to use an amount of basic cesium compound within the range of about 0.001 to about 1.0 mole per mole of symmetric dialkyl carbonate. A more preferred range is from about 0.01 to about 0.1 moles per mole of symmetric carbonate.

The process of the invention is preferably performed in the presence of a cocatalyst selected from the group consisting of crown ethers, polyalkylene glycols, and polyalkylene glycol ethers. These cocatalysts form host-guest complexes with cesium ions, and enhance catalyst basicity. Shorter reaction times and/or higher selectivities to unsymmetric carbonates are possible in the presence of these cocatalysts. For example, the reaction of dimethyl carbonate with tert-butyl alcohol in the presence of cesium carbonate alone (Example 6) gives 43% conversion and 78% selectivity to methyl tert-butyl carbonate (MTBC), while inclusion of polyethylene glycol dimethyl ether (2000 molecular weight) improves MTBC selectivity to 95% (Example 18). Suitable crown ethers include, for example, 18-crown-6, 21-crown-7, dibenzo-18-crown-6, dibenzo-21-crown-7, dibenzo-30-crown-10, polymers that contain crown ether moieties, and the like. Suitable polyalkylene glycols and glycol ethers include polyethylene glycols, polypropylene glycols, and aryl and alkyl ethers derived therefrom. The amount of cocatalyst is preferably within the range of about 0.1 to about 10 moles per mole of basic cesium compound, more preferably from about 0.5 to about 2 moles per mole of cesium compound.

The process of the invention can be performed at any desired temperature, but it is preferred to use a reaction temperature within the range of about 20° C. to about 250° C. A more preferred range is from about 75° C. to about 150° C; most preferred is the range from about 100° C. to about 135° C.

The process of the invention can be performed at, above, or below atmospheric pressure. Batch, semi-batch, and continuous processes can be used. If desired, the reaction can be performed in a moisture-free, inert atmosphere under nitrogen, argon, or the like. Non-reactive organic solvents can be used if desired, but it is often possible and desirable to perform the process in the absence of a solvent. The alcohol, which is preferably used in excess, conveniently serves as a solvent for the process.

The unsymmetric dialkyl carbonate product can be isolated in any desired manner. Volatile unsymmetric carbonates are often conveniently purified by distillation at or below atmospheric pressure. Distillation is also advantageously used in the process to remove volatile alcohol by-products derived from the symmetric dialkyl carbonate reactant. For example, when dimethyl carbonate or diethyl carbonate is the symmetric dialkyl carbonate, methanol or ethanol is a by-product of the process, and either is easily removed by distillation. Removal of alcohol by-products helps drive the reaction in favor of high yields of the unsymmetric dialkyl carbonate.

In a preferred embodiment of the invention, a symmetric dialkyl carbonate having $C_1$-$C_4$ alkyl groups reacts with a tertiary $C_4$-$C_6$ aliphatic alcohol in the presence of a basic cesium compound to produce an unsymmetric carbonate of the formula $R_1O$—CO—$OR_2$ in which R is a $C_1$-$C_4$ alkyl group, and $R_2$ is a tertiary $C_4$-$C_6$ alkyl group. For example, dimethyl carbonate reacts with tert-butyl alcohol in the presence of cesium carbonate to give methyl tert-butyl carbonate. Similarly, diethyl carbonate reacts with tert-amyl alcohol in the presence of cesium oxide to give ethyl tert-amyl carbonate.

The following examples merely illustrate the invention. Those skilled in the art will recognize numerous variations that are within the spirit of the invention and scope of the claims.

EXAMPLES 1–24

Preparation of Methyl tert-Butyl Carbonate from Dimethyl Carbonate and tert-Butyl Alcohol using Basing Cesium Compounds The catalyst and optional cocatalyst (see Table 1 for identity and amounts) are combined in a Fisher-Porter bottle with dimethyl carbonate (2 g) and tert-butyl alcohol (10 g). The bottle is sealed, and the magnetically stirred mixture is heated at 125° C. for 5 h. The reaction products are analyzed by gas chromatography. Conversions of dimethyl carbonate and percent selectivity to methyl tert-butyl carbonate appear in Table 1.

As shown in Table 1, lithium carbonate, sodium carbonate, and potassium carbonate are ineffective transesterification catalysts for the conversion of dimethyl carbonate to methyl tert-butyl carbonate using tert-butyl alcohol (see Comparative Examples 1–3). Surprisingly, switching to cesium carbonate remarkably improves conversion of dimethyl carbonate and selectivity to methyl tert-butyl carbonate (Examples 4–6). Examples 7–19 illustrate the effect of various crown ether, polyalkylene glycol, and polyalkylene glycol ether cocatalysts. Cesium oxide (another basic cesium compound) is effective in the process (Examples 20–21), but neutral cesium compounds (Comparative Examples 22–24) are generally ineffective.

The preceding examples are meant only as illustrations; the true metes and bounds of the invention are defined by the following claims.

TABLE 1

Preparation of Methyl t-Butyl Carbonate from Dimethyl Carbonate and t-Butyl Alcohol Using a Basic Cesium Compound

| Ex # | Catalyst (g) | Cocatalyst (g) | % Conv. | MTBC Select. |
|---|---|---|---|---|
| C1 | $Li_2CO_3$ (0.95) | none | 1 | 0 |
| C2 | $Na_2CO_3$ (1.0) | none | 0 | 0 |
| C3 | $K_2CO_3$ (1.0) | none | 6 | 10 |
| 4 | $Cs_2CO_3$ (0.98) | none | 34 | 53 |
| 5 | $Cs_2CO_3$ (4.3) | none | 45 | 42 |
| 6 | $Cs_2CO_3$ (0.10) | none | 43 | 78 |
| 7 | $Cs_2CO_3$ (0.54) | 18-crown-6 (0.49) | 29 | 40 |
| 8 | $Cs_2CO_3$ (0.50) | dibenzo-18-crown-6 (0.59) | 20 | 76 |
| 9 | $Cs_2CO_3$ (0.52) | dibenzo-21-crown-7 | 54 | 72 |
| 10 | $Cs_2CO_3$ (0.20) | dibenzo-21-crown-7 (0.32) | 26 | 72 |
| 11 | $Cs_2CO_3$ (0.23) | dibenzo-30-crown-10 (0.33) | 49 | 68 |
| 12 | $Cs_2CO_3$ (0.50) | poly(dibenzo-18-crown-6 (0.74) | 11 | 31 |
| 13 | $Cs_2CO_3$ (0.20) | PEG-6000 (0.20) | 23 | 73 |
| 14 | $Cs_2CO_3$ (0.50) | PEG-6000 (0.51) | 44 | 57 |
| 15 | $Cs_2CO_3$ (0.51) | PEG-2000 dimethyl ether (0.50) | 54 | 70 |
| 16 | $Cs_2CO_3$ (0.25) | PEG-2000 dimethyl ether (0.24) | 31 | 72 |
| 17 | $Cs_2CO_3$ (0.10) | PEG-2000 dimethyl ether (0.10) | 16 | 82 |
| 18 | $Cs_2CO_3$ (0.11) | PEG-2000 dimethyl ether (0.52) | 43 | 95 |
| 19 | $Cs_2CO_3$ (0.52) | PEG-750/EPS (0.10) | 53 | 70 |
| 20 | $Cs_2O$ (0.57) | none | 33 | 73 |
| 21 | $Cs_2O$ (0.11) | none | 55 | 80 |
| C22 | $Cs_2(C_2O_4)$ (0.25) | none | 2 | 0 |
| C23 | CsCl (0.10) | none | 0 | 0 |

TABLE 1-continued

Preparation of Methyl t-Butyl Carbonate from Dimethyl Carbonate and t-Butyl Alcohol Using a Basic Cesium Compound

| Ex # | Catalyst (g) | Cocatalyst (g) | % Conv. | MTBC Select. |
|---|---|---|---|---|
| C24 | CsBF$_4$ (0.14) | none | 0 | 0 |

Examples C1–C3 and C22–C24 are comparative examples.
Percent conversion of dimethyl carbonate (% Conv.) and selectivity to methyl t-butyl carbonate (MTBC select.) are found by gas chromatography
PEG-6000 = polyethylene glycol, 6000 molecular weight
PEG-2000 dimethyl ether = polyethylene glycol dimethyl ether, 2000 molecular weight
PEG-750/EPS = polyethylene glycol, 750 molecular weight, bound to an expanded, styrene/divinylbenzene polymer matrix

I claim:

1. A process for producing an unsymmetric dialkyl carbonate, said process comprising reacting a symmetric dialkyl carbonate with an alcohol selected from the group consisting of $C_1$–$C_{20}$ linear, branched, and cyclic aliphatic and aromatic alcohols, in the presence of a basic cesium compound either in the absence of or in the presence of a cocatalyst to produce the unsymmetric dialkyl carbonate.

2. The process of claim 1 wherein the symmetric dialkyl carbonate is selected from the group consisting of dimethyl carbonate and diethyl carbonate, and the alcohol is selected from the group consisting of tert-butyl alcohol and tert-amyl alcohol.

3. The process of claim 1 wherein the process is performed in the presence of a cocatalyst selected from the group consisting of crown ethers, polyalkylene glycols, and polyalkylene glycol ethers.

4. The process of claim 1 wherein the basic cesium compound is selected from the group consisting of cesium carbonate, cesium oxide, cesium bicarbonate, cesium hydroxide, and cesium acetate.

5. The process of claim 1 wherein the basic cesium compound is selected from the group consisting of cesium carbonate and cesium oxide.

6. The process of claim 1 wherein the process is performed at a temperature within the range of about 75° C. to about 150° C.

7. The process of claim 1 wherein the amount of basic cesium compound used is within the range of about 0.001 to about 1.0 moles per mole of symmetric dialkyl carbonate.

8. The process of claim 1 wherein the molar ratio of alcohol to symmetric dialkyl carbonate is within the range of about 2 to about 100.

9. A process for producing an unsymmetric dialkyl carbonate, said process comprising reacting a symmetric dialkyl carbonate having $C_1$–$C_4$ alkyl groups with a tertiary $C_4$–$C_6$ aliphatic alcohol in the presence of a basic cesium compound either in the absence of or in the presence of a cocatalyst to produce the unsymmetric dialkyl carbonate.

10. The process of claim 9 wherein the process is performed in the presence of a cocatalyst selected from the group consisting of crown ethers, polyalkylene glycols, and polyalkylene glycol ethers.

11. The process of claim 9 wherein the basic cesium compound is selected from the group consisting of cesium carbonate, cesium oxide, cesium bicarbonate, cesium hydroxide, and cesium acetate.

12. The process of claim 9 wherein the basic cesium compound is selected from the group consisting of cesium carbonate and cesium oxide.

13. The process of claim 9 wherein the process is performed at a temperature within the range of about 75° C. to about 150° C.

14. The process of claim 9 wherein the amount of basic cesium compound used is within the range of about 0.001 to about 1.0 moles per mole of symmetric dialkyl carbonate.

15. The process of claim 9 wherein the molar ratio of alcohol to symmetric dialkyl carbonate is within the range of about 2 to about 100.

16. A process for producing methyl tert-butyl carbonate, said process comprising reacting dimethyl carbonate with tert-butyl alcohol in the presence of a basic cesium compound either in the absence of or in the presence of a cocatalyst to produce methyl tert-butyl carbonate.

17. The process of claim 16 wherein the process is performed in the presence of a cocatalyst selected from the group consisting of crown ethers, polyalkylene glycols, and polyalkylene glycol ethers.

18. The process of claim 16 wherein the basic cesium compound is selected from the group consisting of cesium carbonate, cesium oxide, cesium bicarbonate, cesium hydroxide, and cesium acetate.

19. The process of claim 16 wherein the basic cesium compound is selected from the group consisting of cesium carbonate and cesium acetate.

20. The process of claim 16 wherein the process is performed at a temperature within the range of about 75° C. to about 150° C.

21. The process of claim 16 wherein the amount of basic cesium compound used is within the range of about 0.001 to about 1.0 moles per mole of dimethyl carbonate.

22. The process of claim 16 wherein the molar ratio of tert-butyl alcohol to dimethyl carbonate is within the range of about 2 to about 100.

* * * * *